US008827919B2

(12) United States Patent
Siejko et al.

(10) Patent No.: US 8,827,919 B2
(45) Date of Patent: *Sep. 9, 2014

(54) METHOD AND APPARATUS FOR THIRD HEART SOUND DETECTION

(71) Applicant: Cardiac Pacemakers, Inc., St. Paul, MN (US)

(72) Inventors: Krzysztof Z. Siejko, Maple Grove, MN (US); Gerrard M. Carlson, Houston, TX (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/685,170

(22) Filed: Nov. 26, 2012

(65) Prior Publication Data

US 2013/0085407 A1 Apr. 4, 2013

Related U.S. Application Data

(63) Continuation of application No. 12/283,760, filed on Sep. 16, 2008, now Pat. No. 8,317,717, which is a continuation of application No. 10/746,853, filed on Dec. 24, 2003, now Pat. No. 7,431,699.

(51) Int. Cl.
*A61B 5/02* (2006.01)
*A61B 7/04* (2006.01)
(52) U.S. Cl.
CPC ........................................ *A61B 7/04* (2013.01)
USPC ........................................................ 600/528
(58) Field of Classification Search
None
See application file for complete search history.

(56) References Cited

U.S. PATENT DOCUMENTS

| 3,799,147 | A | * | 3/1974 | Adolph et al. ................ 600/513 |
|---|---|---|---|---|
| 4,220,160 | A | | 9/1980 | Kimball et al. |
| 4,428,380 | A | | 1/1984 | Wong et al. |
| 4,586,514 | A | | 5/1986 | Schlager et al. |
| 4,628,939 | A | | 12/1986 | Little et al. |
| 4,702,253 | A | | 10/1987 | Nappholz et al. |
| 4,796,639 | A | | 1/1989 | Snow et al. |
| 4,905,706 | A | | 3/1990 | Duff et al. |
| 4,967,760 | A | | 11/1990 | Bennett et al. |

(Continued)

FOREIGN PATENT DOCUMENTS

| WO | WO-0156651 A1 | 8/2001 |
|---|---|---|
| WO | WO-2004050178 A1 | 6/2004 |

(Continued)

OTHER PUBLICATIONS

"U.S. Appl. No. 10/334,694, Advisory Action mailed Dec. 18, 2007", 3 pgs.

(Continued)

*Primary Examiner* — Kennedy Schaetzle
(74) *Attorney, Agent, or Firm* — Schwegman Lundberg & Woessner, P.A.

(57) ABSTRACT

A cardiac rhythm management system includes a heart sound detector providing for detection of the third heart sounds (S3). An implantable sensor such as an accelerometer or a microphone senses an acoustic signal indicative heart sounds including the second heart sounds (S2) and S3. The heart sound detector detects occurrences of S2 and starts S3 detection windows each after a predetermined delay after a detected occurrence of S2. The occurrences of S3 are then detected from the acoustic signal within the S3 detection windows.

20 Claims, 7 Drawing Sheets

(56) References Cited

U.S. PATENT DOCUMENTS

| | | |
|---|---|---|
| 4,981,139 A | 1/1991 | Pfohl |
| 5,010,889 A | 4/1991 | Bredesen et al. |
| 5,025,809 A | 6/1991 | Johnson et al. |
| 5,179,947 A | 1/1993 | Meyerson et al. |
| 5,218,969 A | 6/1993 | Bredesen et al. |
| 5,301,679 A | 4/1994 | Taylor |
| 5,337,752 A | 8/1994 | Reeves |
| 5,544,661 A | 8/1996 | Davis et al. |
| 5,554,177 A | 9/1996 | Kieval et al. |
| 5,674,256 A | 10/1997 | Carlson |
| 5,687,738 A | 11/1997 | Shapiro et al. |
| 5,700,283 A | 12/1997 | Salo |
| 5,792,195 A | 8/1998 | Carlson et al. |
| 5,836,987 A | 11/1998 | Baumann et al. |
| 5,860,933 A | 1/1999 | Don Michael |
| 5,935,081 A | 8/1999 | Kadhiresan |
| 6,002,777 A | 12/1999 | Grasfield et al. |
| 6,044,298 A | 3/2000 | Salo et al. |
| 6,044,299 A | 3/2000 | Nilsson |
| 6,058,329 A | 5/2000 | Salo et al. |
| 6,144,880 A | 11/2000 | Ding et al. |
| 6,193,668 B1 | 2/2001 | Chassaing et al. |
| 6,208,900 B1 | 3/2001 | Ecker et al. |
| 6,269,396 B1 | 7/2001 | Shah et al. |
| 6,327,622 B1 | 12/2001 | Jindal et al. |
| 6,351,673 B1 | 2/2002 | Ding et al. |
| 6,360,127 B1 | 3/2002 | Ding et al. |
| 6,409,675 B1 | 6/2002 | Turcott |
| 6,411,840 B1 | 6/2002 | Bardy |
| 6,440,082 B1 | 8/2002 | Joo et al. |
| 6,459,929 B1 | 10/2002 | Hopper et al. |
| 6,477,406 B1 | 11/2002 | Turcott |
| 6,478,746 B2 | 11/2002 | Chassaing et al. |
| 6,480,733 B1 | 11/2002 | Turcott |
| 6,491,639 B1 | 12/2002 | Turcott |
| 6,520,924 B2 | 2/2003 | Lee |
| 6,527,729 B1 | 3/2003 | Turcott |
| 6,542,775 B2 | 4/2003 | Ding et al. |
| 6,575,916 B2 | 6/2003 | Halleck et al. |
| 6,626,842 B2 | 9/2003 | Oka |
| 6,643,548 B1 | 11/2003 | Mai et al. |
| 6,684,103 B2 | 1/2004 | Ding et al. |
| 6,733,464 B2 | 5/2004 | Olbrich et al. |
| 6,792,308 B2 | 9/2004 | Corbucci |
| 6,821,249 B2 | 11/2004 | Casscells, III et al. |
| 6,824,519 B2 | 11/2004 | Narimatsu et al. |
| 7,096,060 B2 | 8/2006 | Arand et al. |
| 7,139,609 B1 | 11/2006 | Min et al. |
| 7,399,277 B2 | 7/2008 | Saidara et al. |
| 7,431,699 B2 | 10/2008 | Siejko et al. |
| 7,480,528 B2 | 1/2009 | Brockway et al. |
| 7,713,213 B2 | 5/2010 | Siejko et al. |
| 7,853,327 B2 | 12/2010 | Patangay et al. |
| 8,065,010 B2 | 11/2011 | Brockway et al. |
| 8,317,717 B2 * | 11/2012 | Siejko et al. .......... 600/528 |
| 2002/0001390 A1 | 1/2002 | Kawaguchi |
| 2002/0035337 A1 | 3/2002 | Oka |
| 2002/0072684 A1 | 6/2002 | Stearns |
| 2002/0147401 A1 | 10/2002 | Oka |
| 2002/0151938 A1 | 10/2002 | Corbucci |
| 2003/0060851 A1 | 3/2003 | Kramer et al. |
| 2003/0092975 A1 | 5/2003 | Casscells, III et al. |
| 2003/0120159 A1 | 6/2003 | Mohler |
| 2003/0144702 A1 | 7/2003 | Yu et al. |
| 2003/0144703 A1 | 7/2003 | Yu et al. |
| 2003/0176896 A1 | 9/2003 | Lincoln et al. |
| 2003/0208240 A1 | 11/2003 | Pastore et al. |
| 2003/0216620 A1 | 11/2003 | Jain et al. |
| 2003/0229289 A1 | 12/2003 | Mohler |
| 2003/0233132 A1 | 12/2003 | Pastore et al. |
| 2004/0106960 A1 | 6/2004 | Siejko et al. |
| 2004/0106961 A1 | 6/2004 | Siejko et al. |
| 2004/0127792 A1 | 7/2004 | Siejko et al. |
| 2004/0267147 A1 | 12/2004 | Sullivan |
| 2004/0267148 A1 | 12/2004 | Arand et al. |
| 2005/0059897 A1 | 3/2005 | Snell et al. |
| 2005/0065448 A1 | 3/2005 | Stahmann et al. |
| 2005/0149136 A1 | 7/2005 | Siejko et al. |
| 2006/0020295 A1 | 1/2006 | Brockway et al. |
| 2006/0030892 A1 | 2/2006 | Kadhiresan et al. |
| 2006/0282000 A1 | 12/2006 | Zhang et al. |
| 2007/0078491 A1 | 4/2007 | Siejko et al. |
| 2007/0213599 A1 | 9/2007 | Siejko et al. |
| 2009/0132000 A1 | 5/2009 | Brockway et al. |
| 2010/0222653 A1 | 9/2010 | Siejko et al. |
| 2011/0077543 A1 | 3/2011 | Patangay et al. |

FOREIGN PATENT DOCUMENTS

| | | |
|---|---|---|
| WO | WO-2004060483 A1 | 7/2004 |
| WO | WO-2006028575 A2 | 3/2006 |
| WO | WO-2006028575 A3 | 3/2006 |

OTHER PUBLICATIONS

"U.S. Appl. No. 10/334,694, Advisory Action mailed Dec. 23, 2008", 3 pgs.

"U.S. Appl. No. 10/334,694, Final Office Action mailed Oct. 1, 2007", 13 pgs.

"U.S. Appl. No. 10/334,694, Final Office Action mailed Oct. 7, 2008", 14 pgs.

"U.S. Appl. No. 10/334,694, Final Office Action mailed Nov. 27, 2009", 13 pgs.

"U.S. Appl. No. 10/334,694, Non-Final Office Action mailed Mar. 18, 2009", 14 pgs.

"U.S. Appl. No. 10/334,694, Non-Final Office Action mailed Mar. 19, 2008", 15 pgs.

"U.S. Appl. No. 10/334,694, Non-Final Office Action mailed Apr. 20, 2007", 12 pgs.

"U.S. Appl. No. 10/334,694, Non-Final Office Action mailed Apr. 30, 2010", 13 pgs.

"U.S. Appl. No. 10/334,694, Non-Final Office Action mailed Nov. 27, 2006", 9 pgs.

"U.S. Appl. No. 10/334,694, Notice of Allowance mailed Mar. 4, 2011", 7 pgs.

"U.S. Appl. No. 10/334,694, Notice of Allowance mailed Oct. 5, 2010", 6 pgs.

"U.S. Appl. No. 10/334,694, Response filed Feb. 27, 2007 to Non-Final Office Action mailed Nov. 27, 2006", 20 pgs.

"U.S. Appl. No. 10/334,694, Response filed Mar. 1, 2010 to Final Office Action mailed Nov. 27, 2009", 21 pgs.

"U.S. Appl. No. 10/334,694, Response filed Jun. 19, 2008 to Non-Final Office Action mailed Mar. 19, 2008", 20 pgs.

"U.S. Appl. No. 10/334,694, Response filed Jul. 17, 2009 to Non Final Office Action mailed Mar. 18, 2009", 18 pgs.

"U.S. Appl. No. 10/334,694, Response filed Jul. 20, 2007 to Non-Final Office Action mailed Apr. 20, 2007", 18 pgs.

"U.S. Appl. No. 10/334,694, Response filed Jul. 27, 2010 to Non Final Office Action mailed Apr. 30, 2010", 19 pgs.

"U.S. Appl. No. 10/334,694, Response filed Dec. 3, 2007 to Final Office Action mailed Oct. 1, 2007", 21 pgs.

"U.S. Appl. No. 10/334,694, Response filed Dec. 8, 2008 to Final Office Action mailed Oct. 7, 2008", 18 pgs.

"U.S. Appl. No. 10/746,853, Final Office Action mailed May 22, 2007", 11 pgs.

"U.S. Appl. No. 10/746,853, Non-Final Office Action mailed Sep. 26, 2007", 8 pgs.

"U.S. Appl. No. 10/746,853, Non-Final Office Action mailed Dec. 19, 2006", 10 pgs.

"U.S. Appl. No. 10/746,853, Notice of Allowance mailed May 30, 2008", 4 pgs.

"U.S. Appl. No. 10/746,853, Response filed Jan. 17, 2008 to Non-Final Office Action mailed Sep. 26, 2007", 18 pgs.

"U.S. Appl. No. 10/746,853, Response filed Mar. 15, 2007 to Non-Final Office Action mailed Dec. 19, 2006", 16 pgs.

"U.S. Appl. No. 10/746,853, Response filed Jul. 23, 2007 to Final Office Action mailed May 22, 2007", 16 pgs.

"U.S. Appl. No. 12/283,760, Response filed Jul. 17, 2012 to Final Office Action mailed Apr. 24, 2012", 12 pgs.

(56) References Cited

OTHER PUBLICATIONS

"U.S. Appl. No. 12/283,760, Final Office Action mailed Apr. 24, 2012", 16 pgs.

"U.S. Appl. No. 12/283,760, Non Final Office Action mailed Oct. 5, 2011", 9 pgs.

"U.S. Appl. No. 12/283,760, Notice of Allowance mailed Jul. 25, 2012", 5 pgs.

"U.S. Appl. No. 12/283,760, Response filed Feb. 6, 2012 to Non Final Office Action mailed Oct. 5, 2011", 15 pgs.

"European Application Serial No. 05806944.4, Office Action mailed Apr. 14, 2008", 8 pgs.

"European Application Serial No. 05806944.4, Response filed Oct. 17, 2008 to Office Action mailed Apr. 14, 2008", 22 pgs.

"European Application Serial No. 10173334.3, Examination Notification Art. 94(3) mailed Aug. 24, 2011", 4 pgs.

"European Application Serial No. 10173334.3, Office Action Response mailed Jan. 2, 2012", 10 pgs.

"International Application Serial No. PCT/US2005/025235, International Search Report and Written Opinion mailed Apr. 4, 2006", 20 pgs.

"International Application Serial No. PCT/US2005/025235, Invitation to Pay Additional Fees and Partial Search Report mailed Jan. 27, 2006", 9 pgs.

Aaron, S. D, et al., "How accurate is spirometry at predicting restrictive pulmonary impairment?", Chest, 115(3), XP002362629 ISSN: 0012-3692, (Mar. 1999), 869-873.

Kadhiresan, Veerichetty, et al., "Cardiopulmonary Functional Status Assessment Via Heart Rate Response Dectection by Implantable Cardiac Device", U.S. Appl. No. 10/914,632, filed Aug. 9, 2004, 18 pgs.

Kinderman, Michael, et al., "Optimizing the AV Delay in DDD Pacemaker Patients with High Degree AV Block: Mitral Valve Doppler Versus Impedance Cardiography", PACE, vol. 20, (Oct. 1997), 2453-2462.

Leonelli, Fabio M, et al., "Systolic and Diastolic Effects of Variable Atroventricular Delay and Patients with Complete Hear Block and Normal Ventricular Function", Amer. J-Cardiology, vol. 80, (Aug. 1, 1997), 294-298.

Maile, Keith R., et al., "A Dual-Use Sensor for Rate Responsive Pacing and Heart Sound Monitoring", U.S. Appl. No. 10/703,175, filed Nov. 6, 2003, 41 pgs.

Maile, Keith R., et al., "Determining a Patient's Posture From Mechanical Vibrations of the Heart", U.S. Appl. No. 10/900,570, filed Jul. 28, 2004, 24 pgs.

Rohling, H., "Radar CFAR Thresholding in Clutter and Multiple Target Situations", IEEE Trans. Aerosp. Electron. Syst., vol. AES-19, No. 4, (Jul. 1983), 608-621.

Rohling, H., "Some radar topics: waveform design, range CFAR and target recognition", NATO Advanced Study Institute, Advances in Sensing with Security Applications, (2005), 1-30.

Siejko, K. Z., et al., "Method for Correction of Posture Dependence on Heart Sounds", U.S. Appl. No. 11/037,275, filed Jan. 18, 2005, 26 pgs.

Siejko, Krzysztof Z., "A Third Heart Sound Activity Index for Heart Failure Monitoring", U.S. Appl. No. 10/746,874, filed Dec. 24, 2003, 41 pgs.

Siejko, Krzysztof Z., et al., "Method and Apparatus for Third Heart Sound Detection", U.S. Appl. No. 10/746,853, filed Dec. 24, 2003, 40 pgs.

Tavel, Morton E, "The Appearance of Gallop Rhythm after Exercise Stress Testing", Clin. Cardiol., vol. 19, (1996), 887-891.

\* cited by examiner

METHOD AND APPARATUS FOR THIRD HEART SOUND DETECTION

CROSS-REFERENCE TO RELATED APPLICATIONS

This application is a continuation of U.S. patent application Ser. No. 12/283,760, filed Sep. 16, 2008, now issued as U.S. Pat. No. 8,317,717, which is a continuation of U.S. patent application Ser. No. 10/746,853, filed Dec. 24, 2003, now issued as U.S. Pat. No. 7,431,699, which are hereby incorporated by reference in their entirety.

This application is related to co-pending, commonly assigned U.S. patent application Ser. No. 10/746,874, entitled "A THIRD HEART SOUND ACTIVITY INDEX FOR HEART FAILURE MONITORING," filed on Dec. 24, 2003, now U.S. Pat. No. 7,115,096, U.S. patent application Ser. No. 10/334,694, entitled "METHOD AND APPARATUS FOR MONITORING OF DIASTOLIC HEMODYNAMICS," filed Dec. 30, 2002, now issued as U.S. Pat. No. 7,972,275, and U.S. patent application Ser. No. 10/307,896, "PHONOCARDIOGRAPHIC IMAGE-BASED ATRIOVENTRICULAR DELAY OPTIMIZATION," filed Dec. 12, 2002, now issued as U.S. Pat. No. 7,123,962, all assigned to Cardiac Pacemakers, Inc., which are hereby incorporated by reference in their entirety.

TECHNICAL FIELD

This document relates generally to cardiac rhythm management systems and particularly, but not by way of limitation, to such a system sensing and analyzing heart sounds for monitoring, diagnosis, and therapy control.

BACKGROUND

The heart is the center of a person's circulatory system. It includes a complex electro-mechanical system performing two major pumping functions. The left portions of the heart draw oxygenated blood from the lungs and pump it to the organs of the body to provide the organs with their metabolic needs for oxygen. The right portions of the heart draw deoxygenated blood from the organs and pump it into the lungs where the blood gets oxygenated. These mechanical pumping functions are accomplished by contractions of the myocardium (heart muscles). In a normal heart, the sinoatrial (SA) node, the heart's natural pacemaker, generates electrical impulses, called action potentials, that propagate through an electrical conduction system to various regions of the heart to excite myocardial tissues in these regions. Coordinated delays in the propagations of the action potentials in a normal electrical conduction system cause the muscles in various regions of the heart to contract in synchrony such that the pumping functions are performed efficiently. The normal pumping functions of the heart, or the normal hemodynamic performance, require a normal electrical system to generate the action potentials and deliver them to designated portions of the myocardium with proper timing, a normal myocardium capable of contracting with sufficient strength, and a normal electro-mechanical association such that all regions of the heart are excitable by the action potentials.

Electrocardiography (ECG) is known to indicate the functions of the electrical system by allowing monitoring of the action potentials at various portions of the heart. Heart sounds, or generally energies resulted from the heart's mechanical vibrations, indicate the heart's mechanical activities. Measurements performed with simultaneously recorded ECG and heart sounds provide for quantitative indications of the electro-mechanical association.

One type of heart sound, known as the third heart sound, or S3, is known as an indication of heart failure. A heart failure patient suffers from an abnormal electrical conduction system with excessive conduction delays and deteriorated heart muscles that result in asynchronous and weak heart contraction, and hence, reduced pumping efficiency, or poor hemodynamic performance. While the ECG of a heart failure patient may show excessive delays and/or blockages in portions of the electrical conduction system, S3 indicates his or her heart's abnormal mechanical functions. For example, an increase in S3 activity is known to be an indication of elevated filing pressures, which may result in a state of decompensated heart failure. Additionally, S3 amplitude is also related to filing pressures of the left ventricle during diastole. The pitch, or fundamental frequency, of S3 is related to ventricular stiffness and dimension. Chronic changes in S3 amplitude are correlated to left ventricular chamber stiffness and degree of restrictive filling. Such parameters indicate abnormal cardiac conditions, including degrees of severity, and need of appropriate therapies.

For these and other reasons, there is a need for a system providing for S3 detection and analysis.

SUMMARY

A cardiac rhythm management system includes a heart sound detector providing for detection of the third heart sounds (S3). An implantable sensor such as an accelerometer or a microphone senses an acoustic signal indicative heart sounds including the second heart sounds (S2) and S3. The heart sound detector detects occurrences of S2 and starts S3 detection windows each after a predetermined delay after a detected occurrence of S2. The occurrences of S3 are then detected from the acoustic signal within the S3 detection windows.

In one embodiment, a heart sound detection system includes a cardiac signal input, an acoustic signal input, and a heart sound detector. The cardiac signal input receives a cardiac signal indicative of ventricular events. The acoustic signal input receives an acoustic signal indicative of at least S2 and S3. The heart sound detector includes an S2 window generator, an S2 detector, an S3 window generator, and an S3 detector. The S2 window generator generates an S2 window after a predetermined delay starting with each of the ventricular events. The S2 detector detects S2 during the S2 windows. The S3 window generator generates an S3 window after a predetermined delay starting with each of the detected S2. The S3 detector detects S3 during the S3 windows.

In one embodiment, a heart sound detection method provides for S3 detection. A cardiac signal indicative of ventricular events and an acoustic signal indicative of at least S2 and S3 are received. S2 are detected by comparing the acoustic signal to an S2 threshold. An S3 window is generated after a first predetermined delay starting with each of the detected S2. S3 are detected during the S3 window by comparing the acoustic signal to a dynamically adjustable S3 threshold.

In one embodiment, an implantable cardiac rhythm management system includes an implantable lead, an implantable acoustic sensor, and an implantable medical device. The implantable lead is used for sensing a cardiac signal indicative of ventricular events. The implantable acoustic sensor is used to sense an acoustic signal indicative of at least S2 and S3. The implantable medical device includes a cardiac signal input to receive the cardiac signal, an acoustic signal input to receive the acoustic signal, and a heart sound detector to detect S2 and S3. The heart sound detector includes an S2 window generator, an S2 detector, an S3 window generator, and an S3 detector. The S2 window generator generates an S2 window after a predetermined delay starting with each of the ventricular events. The S2 detector detects S2 during the S2 windows. The S3 window generator generate an S3 window after another predetermined delay starting with each of the detected S2. The S3 detector to detect S3 during the S3 windows.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof, each of which are not to be taken in a limiting sense. The scope of the present invention is defined by the appended claims and their equivalents.

BRIEF DESCRIPTION OF THE DRAWINGS

In the drawings, which are not necessarily drawn to scale, like numerals describe similar components throughout the several views. The drawings illustrate generally, by way of example, but not by way of limitation, various embodiments discussed in the present document.

DETAILED DESCRIPTION

Figure 1:
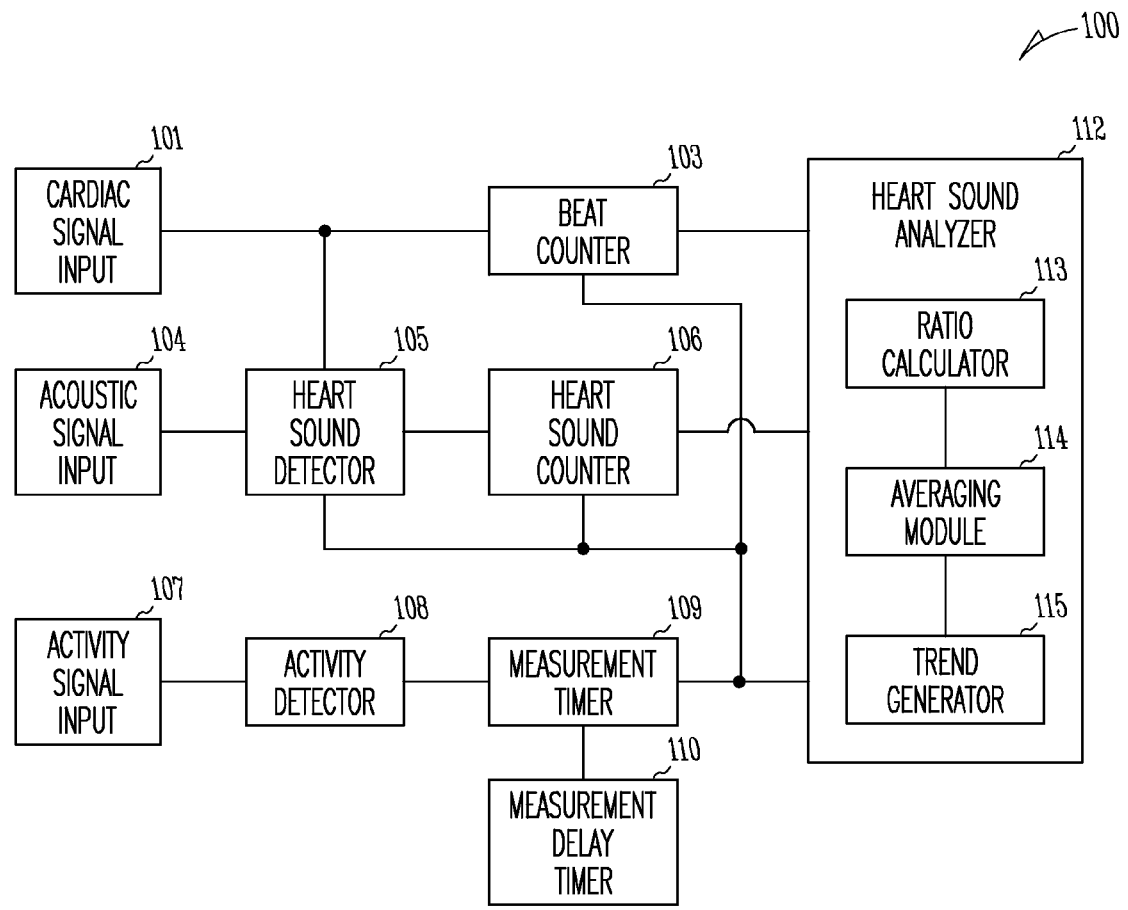
FIG. 1 is a block diagram illustrating an embodiment of a heart sound processing system for trending an S3 index.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. The following detailed description provides examples, and the scope of the present invention is defined by the appended claims and their equivalents.

It should be noted that references to "an", "one", or "various" embodiments in this disclosure are not necessarily to the same embodiment, and such references contemplate more than one embodiment.

This document discusses, among other things, a cardiac rhythm management system monitoring and analyzing heart sounds, particularly the third heart sounds (S3), that are indicative of a heart's mechanical events related to the heart's pumping functions and hemodynamic performance to allow, among other things, diagnosis of cardiac conditions and selection of therapies treating the cardiac conditions. The cardiac rhythm management systems include systems having, for example, pacemakers, cardioverter/defibrillators, pacemaker/defibrillators, cardiac resynchronization therapy (CRT) devices, and cardiac remodeling control devices. However, it is to be understood that the present methods and apparatuses may be employed in other types of medical devices, including, but not being limited to, drug delivery systems and various types of cardiac monitoring devices.

More particularly, the cardiac rhythm management system discussed in this document generates and trends an S3 index indicative of S3 activity. The S3 index (or prevalence) is a ratio of the number of heart beats during which S3 are detected ("S3 beats") to the number of all the heart beats. Because the S3 activity varies throughout the day, the S3 beats are counted for a plurality of measurement sessions distributed over a measurement period. The S3 index is then calculated for the measurement period and trended over multiple measurement periods. A trend of the S3 index provides for an indication of heart failure. For example, an increase in the trend of the S3 index may be indicative of abnormally restrictive filling and elevated filling pressures that lead to edema.

While this document particularly relates to S3, other hearts sounds are also detected and/or analyzed for S3 detection and other purposes. Known and studied heart sounds include the "first heart sound" or S1, the "second heart sound" or S2, the "third heart sound" or S3, the "fourth heart sound" or S4, and their various sub-components. S1 is known to be indicative of, among other things, mitral valve closure, tricuspid valve closure, and aortic valve opening. S2 is known to be indicative of, among other things, aortic valve closure and pulmonary valve closure. S3 is known to be a ventricular diastolic filling sound often indicative of certain pathological conditions including heart failure. S4 is known to be a ventricular diastolic filling sound resulted from atrial contraction and is usually indicative of pathological conditions. The term "heart sound" hereinafter refers to any heart sound (e.g., S1) and any components thereof (e.g., M1 component of S1, indicative of Mitral valve closure).

Throughout this document, "heart sound" includes audible and inaudible mechanical vibrations caused by cardiac activity that can be sensed with an accelerometer. Accordingly, when a mechanical sensor such as an accelerometer is used to sense the heart sounds, the scope of energy included in the sensed "acoustic signal" extends to energies associated with such mechanical vibrations. Unless noted otherwise, S1 refers to the first heart sound, S2 refers to the second heart sound, S3 refers to the third heart sound, and S4 refers to the fourth heart sounds, each as a heart sound type, or as one or more occurrences of the corresponding type heart sounds, depending on the context. A "heart beat" includes a cardiac cycle. An "S3 beat" includes a cardiac cycle during which S3 is detected. An "S3 index," also referred to as an "S3 ratio," includes a ratio of the number of the S3 beats to the number of the total heart hearts, both detected during the same time period.

Throughout this document, a "user" includes a physician or other caregiver who examines and/or treats a patient using one or more of the methods and apparatuses reported in the present document.

FIG. 1 is a block diagram illustrating an embodiment of a heart sound processing system 100 for trending the S3 index. Heart sound processing system 100 trends the S3 index by calculating an average ratio of the number of S3 beats to the total number of heart beats counted over predetermined measurement sessions. It includes a cardiac signal input 101, a beat counter 103, an acoustic signal input 104, a heart sound detector 105, a heart sound counter 106, an activity signal input 107, an activity detector 108, a measurement timer 109, a measurement delay timer 110, and a heart sound analyzer 112.

Cardiac signal input 101 receives cardiac signals indicative of cardiac events such as atrial and ventricular contractions. The cardiac signals include electrocardiographic (ECG) signals and/or event markers indicative of occurrences and timing of the cardiac events. In one embodiment, cardiac signal input 101 receives at least one ventricular electrogram (intracardiac ECG) acquired through at least one intracardiac electrode coupled to an implantable device. The ventricular electrogram is indicative of intrinsic ventricular events (sensed R-waves) and paced ventricular events (ventricular pacing pulses and/or paced R-waves). In another embodiment, cardiac signal input 101 receives at least one signal including event markers indicative of occurrences and timing of intrinsic and paced ventricular events. The intrinsic and paced ventricular events provide for heart beat detection and counting and serve as a timing reference for heart sound detections, as discussed below with reference to FIGS. 2 and 3.

Beat counter 103 counts the number of detected heart beats. In one embodiment, beat counter 103 counts one beat for each intrinsic or paced ventricular event.

Acoustic signal input 104 receives an acoustic signal indicative of one or more types of heart sounds including at least S3. In one embodiment, the acoustic signal is acquired by a microphone sensing acoustic energies generated by mechanical vibrations of the heart. In another embodiment, the acoustic signal is acquired by an accelerometer sensing energies associated with the mechanical vibrations of the heart, including both audible and inaudible energies. In one further embodiment, the acoustic signal is a rectified and low-pass filtered signal, such as an acoustic signal 340 illustrated in FIG. 3.

Heart sound detector 105 detects at least S3 from the acoustic signal received by acoustic signal input 104. In one embodiment, heart sound detector also detects 51 and/or S2 during the process of detecting S3. Heart sound detector 105 is further discussed below with reference to FIG. 2.

Heart sound counter 106 counts the number of S3 beats. During each counted heart beat, if heart sound detector 105 detects an S3, heart sound counter 106 counts one S3 beat.

Activity signal input 107 detects a physical activity level of a person from whom the heart sounds are detected. When the acoustic signal is acquired by an accelerometer, physical activities may be sensed as a noise because the accelerometer senses both the heart's vibrations and the person's gross bodily movements. The physical activity level thus determines whether the heart sounds can be reliably detected, i.e., without detecting the person's gross activities as heart sounds.

Activity detector 108 determines whether the physical activity level exceeds a threshold above which heart sound detection is considered unreliable. In one embodiment, activity detector 108 includes a comparator to compare the physical activity level to a predetermined threshold. Activity detector 108 generates a permission signal when the physical activity level is below the threshold.

Measurement timer 109 starts and times measurement sessions during which the heart beats and the S3 beats are counted. In one embodiment, measurement timer 109 includes a measurement period timer and a measurement timer. Each measurement period includes a plurality of measurement sessions each start at prescheduled times. In one embodiment, adjacent measurement periods overlap. For example, measurement period M includes predetermined measurement sessions N, N+1, and N+2; measurement period M+1 includes predetermined measurement sessions N+1, N+2, and N+3; and so on. In another embodiment, measurement periods do not overlap. For example, measurement period M includes measurement sessions N, N+1, and N+2; measurement period M+1 includes measurement sessions N+3, N+4, and N+5; and so on. In one embodiment, a user determines and programs the timing of the measurement periods and the timing of the measurement sessions. In one specific embodiment, the user makes the determination based on the need and the conditions of a particular patient. In one embodiment, measurement timer 109 includes a measurement period clock to time a predetermined time interval as one measurement period. In another embodiment, measurement timer 109 includes a measurement period counter to count a predetermined number of measurement sessions as a measurement period. In one embodiment, measurement timer 109 includes a measurement session clock to time a predetermined time interval as one measurement session. In another embodiment, measurement timer 109 includes a measurement session counter to count a predetermined number of heart beats as one measurement session. Measurement timer 109 starts a measurement session only when the output of activity detector 108 represents a permission signal. In one specific embodiment, the measurement period is one day and includes about 4 to 48 measurement sessions, depending on the patient's circumstances, and each measurement session lasts for about 10 to 30 beats.

Measurement delay timer 110 delays the start of a measurement session when a scheduled measurement session is prevented from starting by an absence of the permission signal. In one embodiment, measurement delay timer 110 delays the start of a measurement session until the permission signal is given by activity detector 108. In another embodiment, measurement delay timer 110 checks the presence of the permission signal periodically with a predetermined delay period, and allows the start of a measurement session when the permission signal is present at the end of one of the predetermined delay periods.

Heart sound analyzer 112 generates a trend of S3 index based on a ratio of the number of S3 beats to the number of total heart beats counted during a predetermined time period (the S3 index or S3 ratio). In one embodiment, the ratio is expressed as a percentage (the S3 percentage). Heart sound analyzer 112 includes a ratio calculator 113, an averaging module 114, and a trend generator 115. In one embodiment, ratio calculator 113 receives the number of the S3 beats and the number of the heart beats counted during each measurement session and calculate the S3 ratio for each measurement session, resulting in an S3 session ratios (i.e., S3 indexes for the measurement sessions). In one specific embodiment, ratio calculator 113 includes a percentage calculator to calculate the S3 percentage for the measurement session, resulting in S3 session percentages. In another embodiment, ratio calculator 113 estimates the S3 ratio for each measurement session based on some but not all the beats (such as every other beat), for example, when detecting and/or counting each and every beat and/or S3 beat is impractical. Averaging module 114 calculates an average of the S3 session ratios over each measurement period to result in S3 periodic ratios (i.e., S3 indexes for the measurement periods). Trend generator 115 generates the trend of S3 index as a moving S3 periodic ratio over a plurality of the measurement periods, where each S3 periodic ratio is an average of the S3 session ratios for one of the measurement periods. In an alternative embodiment, ratio calculator 113 receives the number of the S3 beats and the number of the heart beats counted during each measurement period and calculate the S3 ratio for that measurement period, directly resulting in S3 periodic ratios. Trend generator 115 generates the trend of S3 index as a moving S3 periodic ratio over a plurality of the measurement periods. In one embodiment, trend generator 115 generates the trend of S3 index as a plot of daily S3 ratios over multiple days.

Figure 2:
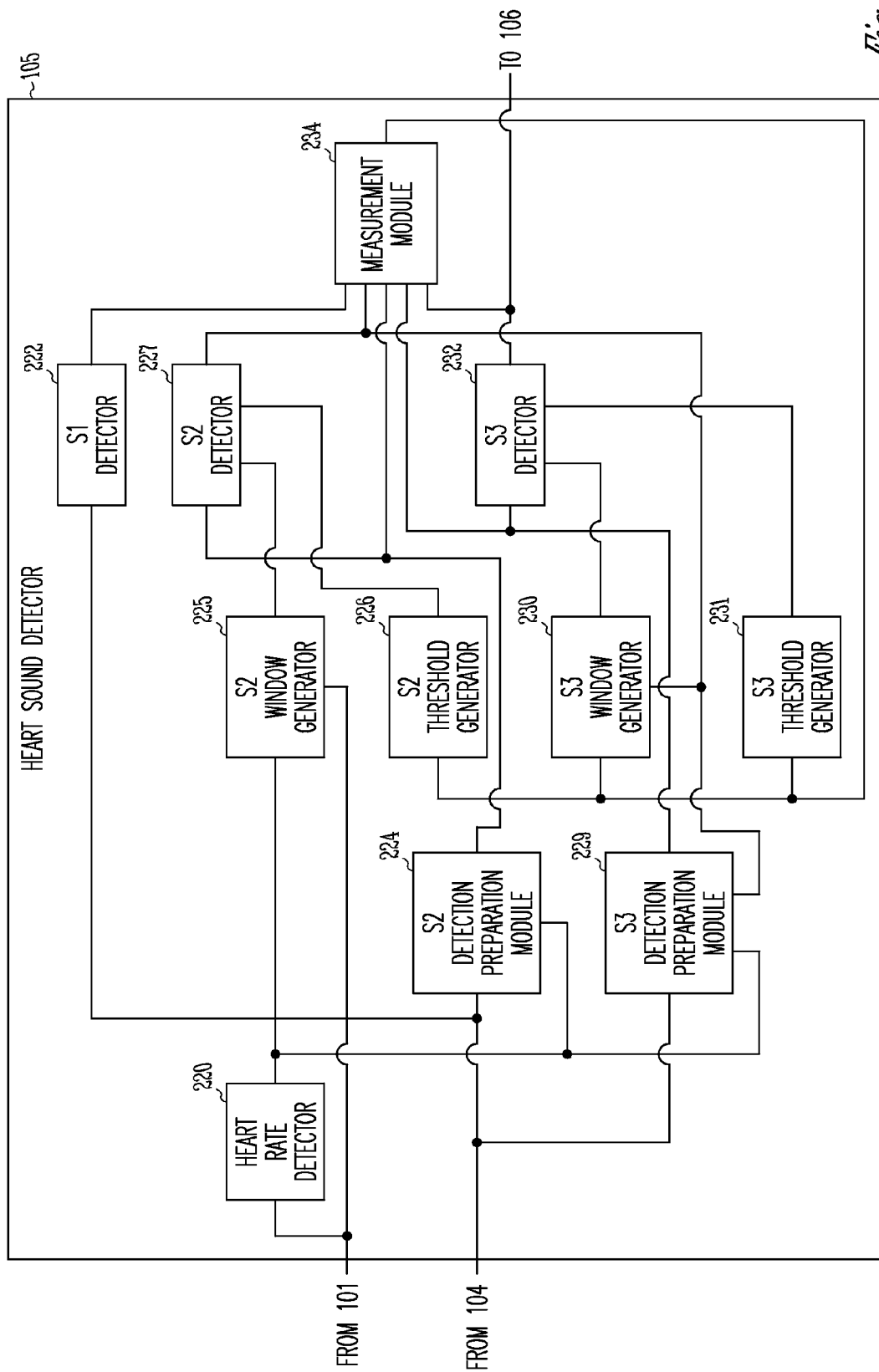
FIG. 2 is a block diagram illustrating an embodiment of a heart sound detector.
Figure 3:
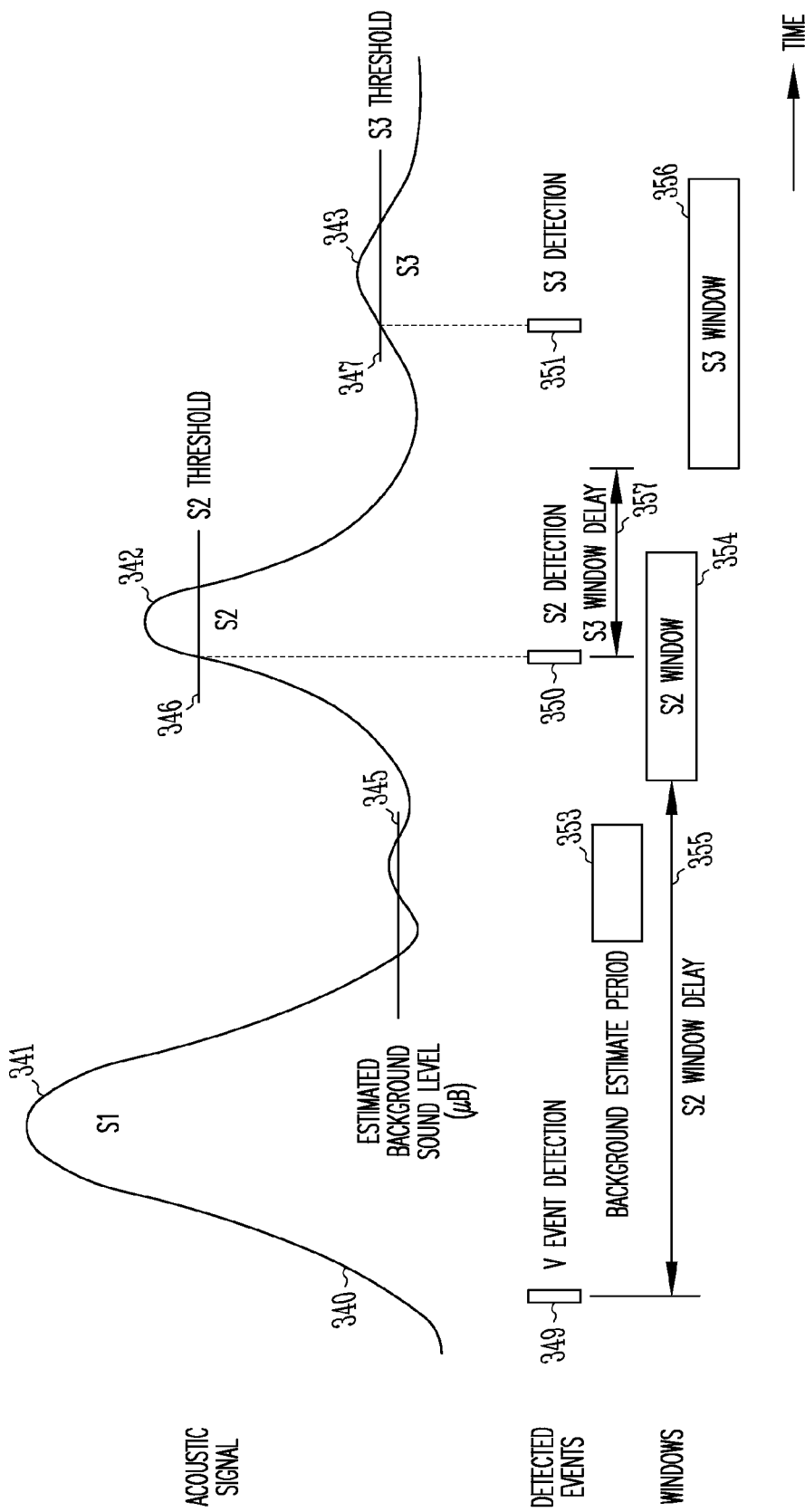
FIG. 3 is an illustration of an embodiment of a method for detecting selected heart sounds.

FIG. 2 is a block diagram illustrating an embodiment of heart sound detector 105. Heart sound detector 105 detects S3 by using the method illustrated in FIG. 3. FIG. 3 shows an acoustic signal 340 indicative of an S1 occurrence 341, an S2 occurrence 342, and an S3 occurrence 343 during one cardiac cycle. In one embodiment, acoustic signal 340 represents an output signal of an envelope detector that rectifies and low-pass filters a sensor signal indicative of heart sounds. Acoustic input 104 receives acoustic signal 340. In one embodiment, the S3 detection method employed by heart sound detector 105 provides for detection of at least S2 and S3. Detection of S1 is required for the detection of S3 when the amplitude and/or energy of S1 are needed to adjust one or more detection thresholds including an S2 threshold 346 and an S3 threshold 347.

S2 and S3 detections are repeated for each cardiac cycle when the heart sounds are being detected. S2 detection includes comparing the amplitude of acoustic signal 340 to S2 threshold 346 during an S2 window 354. S2 window has a predetermined temporal relationship with a ventricular (V) event detection 349, such as an R-wave or a delivery of a ventricular pacing pulse. As illustrated in FIG. 3, V event detection 349 starts a predetermined S2 window delay 355. S2 window 354 starts when S2 window delay 355 expires. S2 detection occurs when the amplitude of acoustic signal 340 exceeds S2 threshold 346 during S2 window 354. S2 window delay 355 and the duration of S2 window 354 are programmed on a patient-by-patient basis. In one embodiment, the timing of S2 detection 350 is empirically estimated for each individual patient and dynamically adjusted based on the patient's heart rate. In one specific example, the time interval between V event detection 349 and S2 detection 350, $T_{V\text{-}S2}$, is estimated by: $T_{V\text{-}S2}=0.500-0.002HR$ seconds, where HR is heart rate in beats per minute, and 0.500 seconds is empirically derived for the individual patient. Then, the duration of S2 window 354 is empirically derived for that patient, and S2 window 354 is centered at the estimated time for S2 detection 350, i.e., end of $T_{V\text{-}S2}$. S2 window delay is, therefore, $T_{V\text{-}S2}$ minus a half of the duration of S2 window 354.

S3 detection includes comparing the amplitude of acoustic signal 340 to S3 threshold 347 during an S3 window 356. S3 window has a predetermined temporal relationship with S2 detection 350. An S3 window delay 357 starts with S2 detection 350. S3 window 356 starts when S3 window delay 357 expires. S3 detection occurs when the amplitude of acoustic signal 340 exceeds S3 threshold 347 during S3 window 356. S3 window delay 357 and the duration of S3 window 356 are programmed on a patient-by-patient basis. In one embodiment, S3 window delay 357 is programmable between 100 and 200 milliseconds. The duration of S3 window 356 is programmable to about 150 ms but is terminated by V event 349 of the next cardiac cycle it occurs before the end of the programmed duration.

As illustrated in FIG. 2, heart sound detector 105 includes a heart rate detector 220, an S1 detector 222, an S2 detection module (including an S2 detection preparation module, an S2 window generator 225, an S2 threshold generator 226, and an S2 detector 227), an S3 detection module (including an S3 detection preparation module, an S3 window generator 230, an S3 threshold generator 231, and an S3 detector 232), and a measurement module 234. Heart rate detector 220 detects a heart rate from the cardiac signal such as the signal received by cardiac signal input 101.

S1 detector is required when S3 threshold 347 depends at least partially on the S1 amplitude or energy. It is also required when, as part of an overall signal processing and analysis scheme, measurement related to S1 are taken.

S2 detection preparation module 224, S2 window generator 225, S2 threshold generator 226, and S2 detector 227 perform S2 detection. S2 detection preparation module 224 is needed when acoustic signal 340 needs to be further processed to facilitate an accurate S2 detection. In one embodiment, S2 detection preparation module 224 includes an averaging circuit that improves the signal-to-noise ratio of acoustic signal 340 by ensemble averaging. In one specific embodiment, the averaging circuit aligns multiple segments of acoustic signal 340 by V event markers representing V event detection 349 on each segment. The segments of acoustic signal 340 to be included for the ensemble averaging are selected from segments of acoustic signal 340 associated with consecutive cardiac cycles with a relatively constant heart rate (e.g., within about 10 to 20 beats per minute variation). S2 window generator 225 includes an S2 window delay timer to time S2 window delay 355 and an S2 window timer to time S2 window 354. V event detection 349 (represented by such as an event marker include in the cardiac signal) triggers the S2 window delay timer to start timing S2 window delay 355. The expiration of S2 window delay 355 triggers the S2 window timer to time S2 window 354, during which S2 is being detected. S2 threshold generator 226 generates S2 threshold 346 based on the amplitude of S1 and/or the amplitude of S2. In one embodiment, S2 threshold generator 226 dynamically adjusts S2 threshold 346 based on the amplitude of S1 and/or the amplitude of S2 averaged over a moving window including a plurality of heart beats. S2 detector 227 includes a comparator to compare acoustic signal 340 to S2 threshold 346, and detects an occurrence of S2 when the amplitude of acoustic signal 340 exceeds S2 threshold 346 during S2 window 354.

S3 detection preparation module 229, S3 window generator 230, S3 threshold generator 231, and S3 detector 232 perform the S3 detection. S3 detection preparation module 229 is needed when acoustic signal 340 needs to be further processed to facilitate an accurate S3 detection. In one embodiment, S3 detection preparation module 229 includes the averaging circuit of S2 detection preparation module 224, and the averaged acoustic signal is used for both S2 and S3 detection. In one specific embodiment, S3 detection preparation module 229 and S2 detection preparation module 224 includes a single averaging circuit—the same averaging circuit that performs the ensemble averaging discussed above. In another embodiment, S3 detection preparation module 229 includes an averaging circuit for the purpose of S3 detection only. This averaging circuit improves the signal-to-noise ratio of acoustic signal 340 for the S3 detection by an ensemble averaging process. The averaging circuit aligns multiple segments of acoustic signal 340 by S2 markers representing S2 detection 350 on each segment, where the S2 detection 350 is resulted from S2 detection performed on acoustic signal 340 before the ensemble averaging. The segments of acoustic signal 340 to be included for the ensemble averaging are selected from segments of acoustic signal 340 associated with consecutive cardiac cycles with a relatively constant heart rate (e.g., within about 10 to 20 beats per minute variation). S3 window generator 230 includes an S3 window delay timer to time S3 window delay 357 and an S2 window timer to time S3 window 356. S3 detection 350 triggers the S3 window delay timer to start timing S3 window delay 357. The expiration of S3 window delay 357 triggers the S3 window timer to time S3 window 356, during which S3 is being detected. S3 threshold generator 231 generates S3 threshold 347. In one embodiment, S3 threshold generator 231 determines S3 threshold 347 based on one or more of an S1 amplitude and an S2 amplitude. In one specific embodiment, S3 threshold generator 231 determines S3 threshold 347 as a percentage of the S2 amplitude. In another embodiment, S3 threshold generator 231 determines S3 threshold 347 based on a total acoustic energy in one cardiac cycle. The purpose is to normalize S3 threshold 347 by the total acoustic energy, such that the S3 detection remains accurate when external variables causes the amplitude of acoustic signal 340 to shift. The total acoustic energy is calculated by integrating acoustic signal 340 over one cardiac cycle or adding the estimated energies of S1, S2, and S3 (if present). In one specific example, S3 threshold generator 231 determines S3 threshold 347 based on at least a mean and a standard deviation of the total acoustic energy in the cardiac cycle. In another embodiment, S3 threshold generator 231 determines S3 threshold 347 based on a total acoustic energy during systole of one cardiac cycle. The total acoustic energy is calculated by integrating acoustic signal 340 over the time interval between V event detection 349 and the beginning of S3 window 356 or adding the estimated energies of S1 and S2. In one specific embodiment, S3 threshold generator 231 determines S3 threshold 347 based on at least a mean and a standard deviation of the total acoustic energy during systole of the cardiac cycle. In another embodiment, S3 threshold generator 231 determines S3 threshold 347 based on a temporal average of one or more of the S1 amplitude, the S2 amplitude, and the total acoustic energy in one cardiac cycle. In another embodiment, S3 threshold generator 231 determines S3 threshold 347 based on an estimated background sound level 345 ($\mu_B$) measured during a background estimate period 353, which is a predetermined period between S1 and S2, as illustrated in FIG. 3. Background estimate period 353 is centered between $T_{S1max}$ and $T_{S2\ min}$, where $T_{S1max}$ is the latest point in time where S1 energy is expected, and is $T_{S2\ min}$ is the point in time where S2 window 354 begins. In one embodiment, $T_{S1max}$ is empirically estimated based on a patient population. In one embodiment, $T_{S1max}$ is in a range of about 100 to 200 millisecond after V event detection 349. In one embodiment, the duration of background estimate period 353 substantially equals to the time interval between $T_{S1max}$ and $T_{S2\ min}$. In another embodiment, the duration of background estimate period 353 is shorter than the time interval between $T_{S1max}$ and $T_{S2\ min}$. In another embodiment, the duration of background estimate period 353 is set to be equal to the time interval between $T_{S1max}$ and $T_{S2\ min}$ but subjected to a maximum duration and a minimum duration. The duration of background estimate period 353 is set to the maximum duration if the time interval between $T_{S1max}$ and $T_{S2\ min}$ is longer than the maximum duration and to the minimum duration if the time interval between $T_{S1max}$ and $T_{S2\ min}$ is shorter than the minimum duration. In one embodiment, S3 threshold generator 231 scales background estimate period 353 for the detected heart rate. S3 threshold 347 is a function of $\mu_B$. In one specific embodiment, S3 threshold generator 231 sets and dynamically adjusts S3 threshold 347 to $\mu_B*K$, where K is a programmable constant. In one embodiment, K is a constant determined, and can be later adjusted, by a user. In one embodiment, K is a constant false alarm rate (CFAR) as known in the art of signal processing. S3 detector 232 includes a comparator to compare acoustic signal 340 to S3 threshold 347, and detects an occurrence of S3 when the amplitude of acoustic signal 340 exceeds S3 threshold 347 during S3 window 356.

Measurement module 234 measures parameters from detected S1, S2 and/or S3. In one embodiment, the measured parameters are used to set and adjust S2 threshold 346 and/or S3 threshold 347. In another embodiment, the measured parameters are used for various cardiac functional analysis based on or related to heart sounds. In one embodiment, measurement module 234 includes an amplitude detector to detect amplitudes of S1, S2, and/or S3. In one further embodiment, measurement module 234 includes an energy detector to detect energies associated with S1, S2, and/or S3. Examples of other parameters measured by measurement module 234 include, but are not limited to, duration of any type heart sound, fundamental and/or harmonic frequencies of any heart sound, time interval between any two heart sounds, and time interval between an intrinsic or paced cardiac event detected from the electrogram and a heart sound detected from the acoustic signal.

Figure 4:
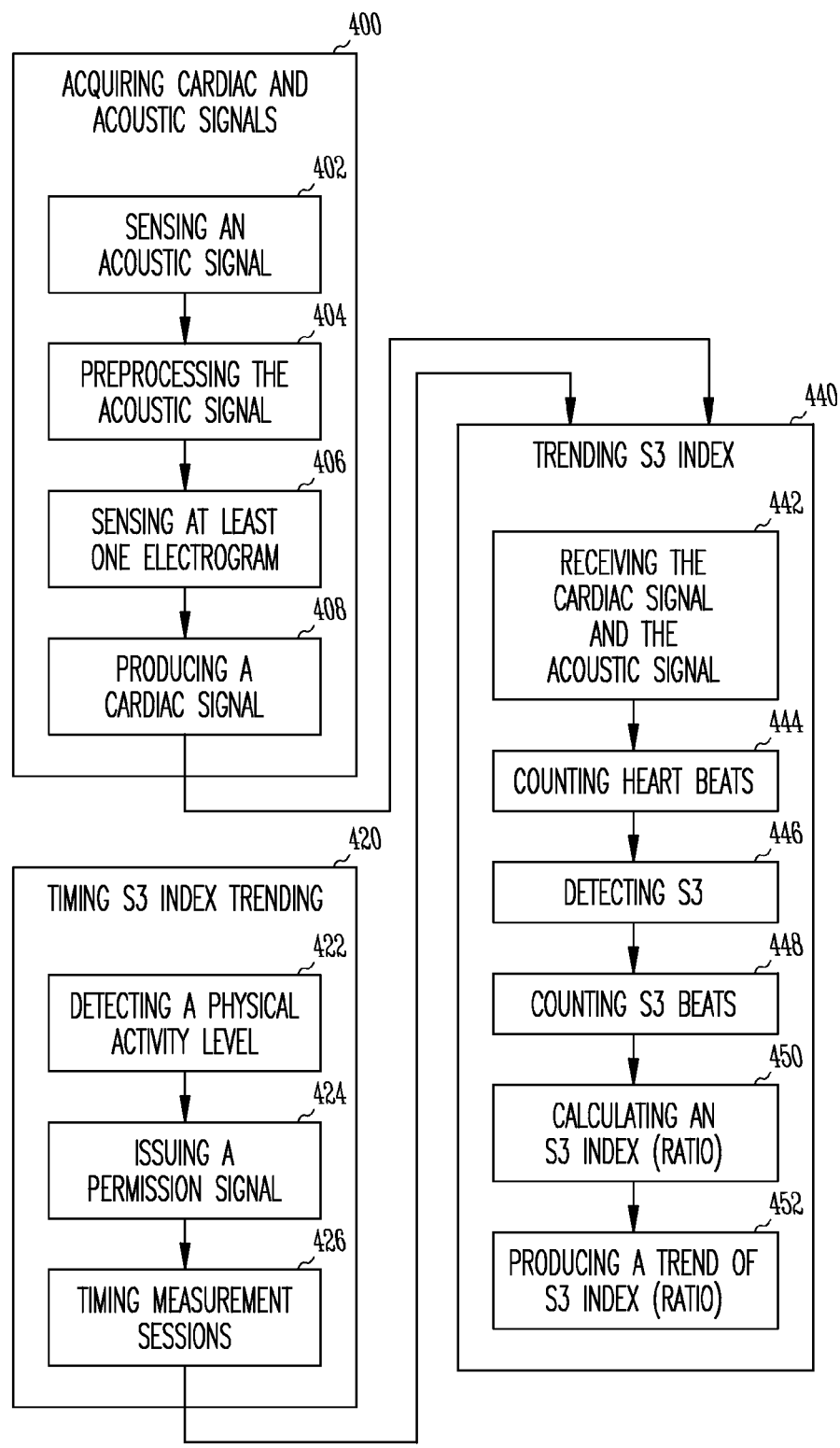
FIG. 4 is a flow chart illustrating an embodiment of a method for trending the S3 index using the system of FIG. 1.

FIG. 4 is a flow chart illustrating an embodiment of a method for trending the S3 index. In one embodiment, the method is performed using heart sound processing system 100. The method includes acquiring cardiac and acoustic signals at 400, timing S3 index trending at 420, and trending the S3 index at 440.

Cardiac and acoustic signals required for trending the S3 index are sensed and preprocessed at 400. At 402, an acoustic signal is sensed. In one embodiment, this includes sensing an audio signal generated from a heart using a microphone placed in or near the heart. In another embodiment, this includes sensing a mechanical vibration of the heart using an accelerometer placed in or near the heart. The acoustic signal is preprocessed at 404. In one embodiment, this includes performing envelope detection, i.e., rectifying and low-pass filtering the sensed acoustic signal. One example of a resultant preprocessed acoustic signal is illustrated as acoustic signal 340 in FIG. 3. At 406, at least one electrogram is sensed. In one embodiment, this includes sensing a ventricular electrogram with at least one electrode placed a ventricular chamber of the heart to sense ventricular events. A cardiac signal is produced at 408. In one embodiment, this includes detecting cardiac events indicated in the sensed electrogram and producing event markers each indicative of an occurrence of the detected cardiac events, including its type and timing. In one specific example, the cardiac signal includes ventricular event markers representing sensed ventricular contractions and/or deliveries of ventricular pacing pulses.

The heart sound analysis producing the trend of the S3 index is a periodic process timed at 420. The timing includes timing measurement periods each including a plurality of measurement sessions. In one embodiment, the measurement period is a predetermined time period defined as a number of hours, days, weeks, etc. Each measurement period includes a plurality of prescheduled measurement sessions. In one embodiment, a physical activity level is detected at 422. The physical activity level indicates a person's gross bodily movements that may interfere with the sensing of the acoustic signal. A permission signal is issued at 424 to allow the start of a measurement session if the physical activity level is below a threshold level indicating that the person is resting. If the permission signal is present when a measurement session is scheduled to begin, a measurement session is timed at 426. In one embodiment, the measurement session is timed as a predetermined period of time. In another embodiment, the measurement session is timed by counting a predetermined number of heart beats. If the permission signal is absent when a measurement session is scheduled to begin, the measurement session is postponed for a predetermined period of time or until the physical activity level falls below the threshold level. In one embodiment, timing S3 index trending at 420 also includes timing the acquisition of the cardiac and acoustic signals.

A trend of the S3 index is produced at 440. The cardiac signal produced at 408 and the acoustic signal preprocessed at 404 are received at 442. Heart beats are counted at 444 for each measurement session or period, based on one type of cardiac events included in the cardiac signal. In one embodiment, one heart beat is counted for each ventricular event. Occurrences of S3 are detected at 446. The S3 beats are counted at 448 for each measurement session or period. The S3 index is calculated at 450, as the ratio of the number of S3 beats to the number of total heart beats counted during the measurement session or period. In one embodiment, the ratio is expressed as a percentage. The trend of the S3 index is produced at 452. In one embodiment, the trend of the S3 index is a moving S3 index calculated for the measurement periods. In another embodiment, the trend of the S3 index is a moving average of the S3 index calculated for the measurement sessions over the measurement periods. In one embodiment, trend of the S3 index is presented as a plot of S3 indices over a measured period or another predetermined period. In one specific embodiment, trend of the S3 index is presented as a plot of daily S3 indices.

Figure 5:
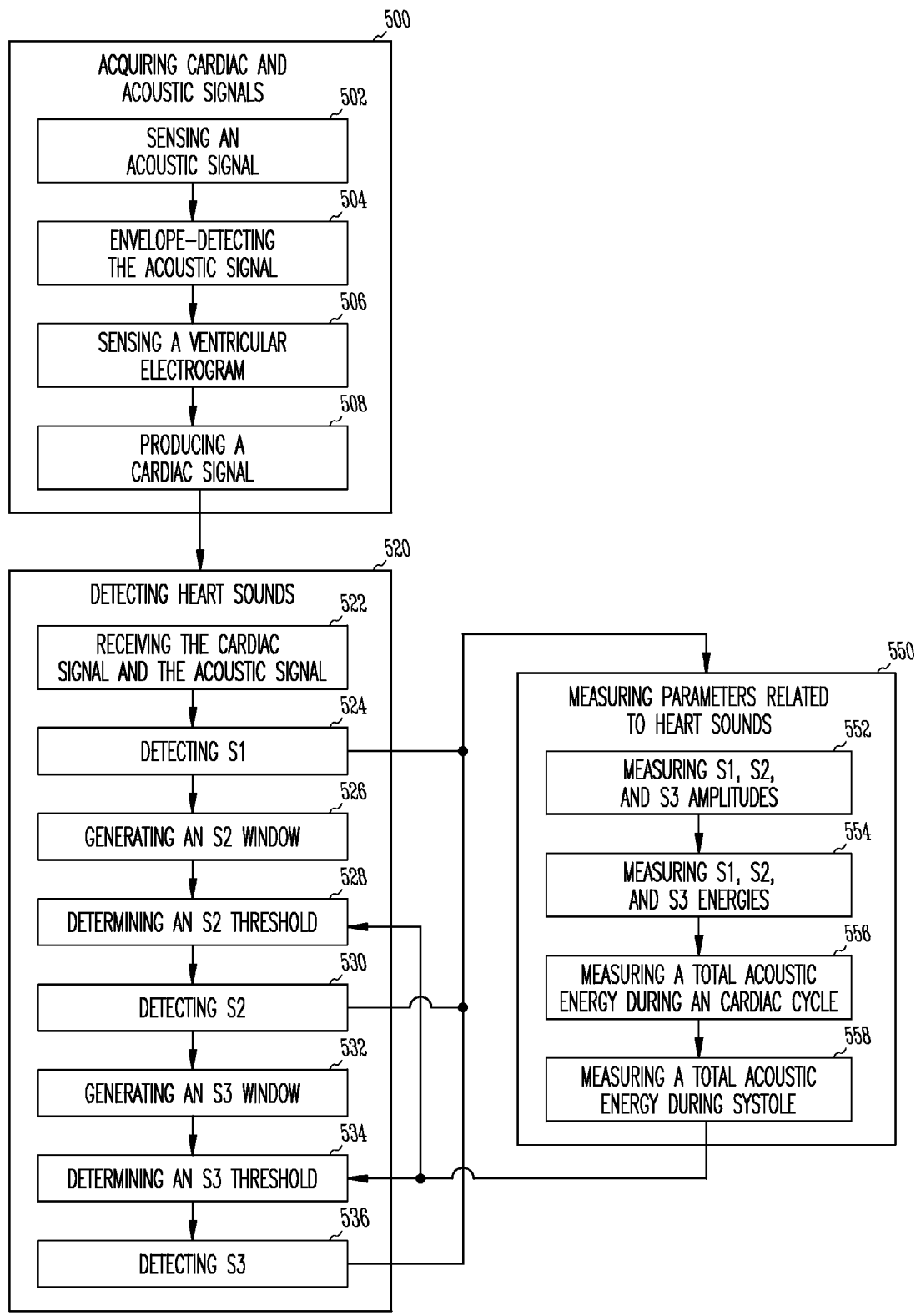
FIG. 5 is a flow chart illustrating an embodiment of a method for detecting S3 using the heart sound detector of FIG. 2.

FIG. 5 is a flow chart illustrating an embodiment of a method for detecting S3. In one embodiment, the method is performed using heart sound detector 105. The method includes acquiring cardiac and acoustic signals at 500, detecting heart sounds at 520, and measuring parameters related to the detected heart sounds at 550.

Cardiac and acoustic signals are sensed and preprocessed at 500. At 502, an acoustic signal is sensed. In one embodiment, this includes sensing an audio signal generated from a heart using a microphone placed in or near the heart. In another embodiment, this includes sensing a mechanical vibration of the heart using an accelerometer placed in or near the heart. The acoustic signal is envelope-detected, i.e., rectified and low-pass filtered, at 504. One example of the envelope-detected acoustic signal is illustrated as acoustic signal 340 in FIG. 3. At 506, a ventricular electrogram is sensed. A cardiac signal is produced at 508. This includes detecting ventricular events, including sensed ventricular contractions and/or deliveries of ventricular pacing pulses, and generating ventricular event markers representing the detected ventricular events. In one embodiment, when the S3 index trending method (illustrated in FIG. 4) employs the S3 detection method (illustrated in FIG. 5), step 400 and step 500 include substantially the same steps.

Heart sounds including S1, S2, and/or S3 are detected at 520. The cardiac signal and the acoustic signal are received at 522. S1 is detected at 524. In one embodiment, detecting S1 includes comparing the amplitude of the preprocessed acoustic signal to an S1 threshold. An S2 window is generated at 526. An S2 threshold is determined at 528. S2 is detected at 530. In one embodiment, steps 526, 528, and 530 are performed using the method discussed above with reference to FIG. 3. An S3 window is generated at 532. An S3 threshold is determined at 534. S3 is detected at 536. In one embodiment, steps 532, 534, and 536 are performed using the method discussed above with reference to FIG. 3.

Parameters are measured from the detected heart sounds at 550. In one embodiment, the parameters are used to determine the S1 threshold, the S2 threshold, and/or the S3 threshold. Amplitudes of S1, S2, and/or S3 are measured at 552. In one embodiment, each amplitude is measured as an average of amplitudes of one type heart sound measured over a plurality of heart beats. Energies associated with S1, S2, and/or S3 are measured at 554. In one embodiment, each energy is measured as an average of energies associated with one type heart sound measured over a plurality of heart beats. A total acoustic energy during a cardiac cycle is measured (and/or calculated) at 556. In one embodiment, the total acoustic energy during the cardiac cycle is measured as an average over a plurality of cardiac cycles (heart beats). A total acoustic energy during systole is measured (and/or calculated) at 558. In one embodiment, the total acoustic energy during systole is measured as an average over a plurality of heart beats.

In one embodiment, one or more parameters measured at 550 are used for analyzing cardiac conditions. One example of such parameter measurement and use is discussed in U.S. patent application Ser. No. 10/334,694, entitled "METHOD AND APPARATUS FOR MONITORING OF DIASTOLIC HEMODYNAMICS," filed Dec. 30, 2002, assigned to Cardiac Pacemakers, Inc., the specification of which is incorporated herein by reference in its entirety.

FIGS. 4 and 5 are for illustrative purposes and do not necessarily reflect the exact temporal order by which the steps are performed in practice. The actual order or sequence by which the steps are performed depends on logic and design considerations.

Figure 6:
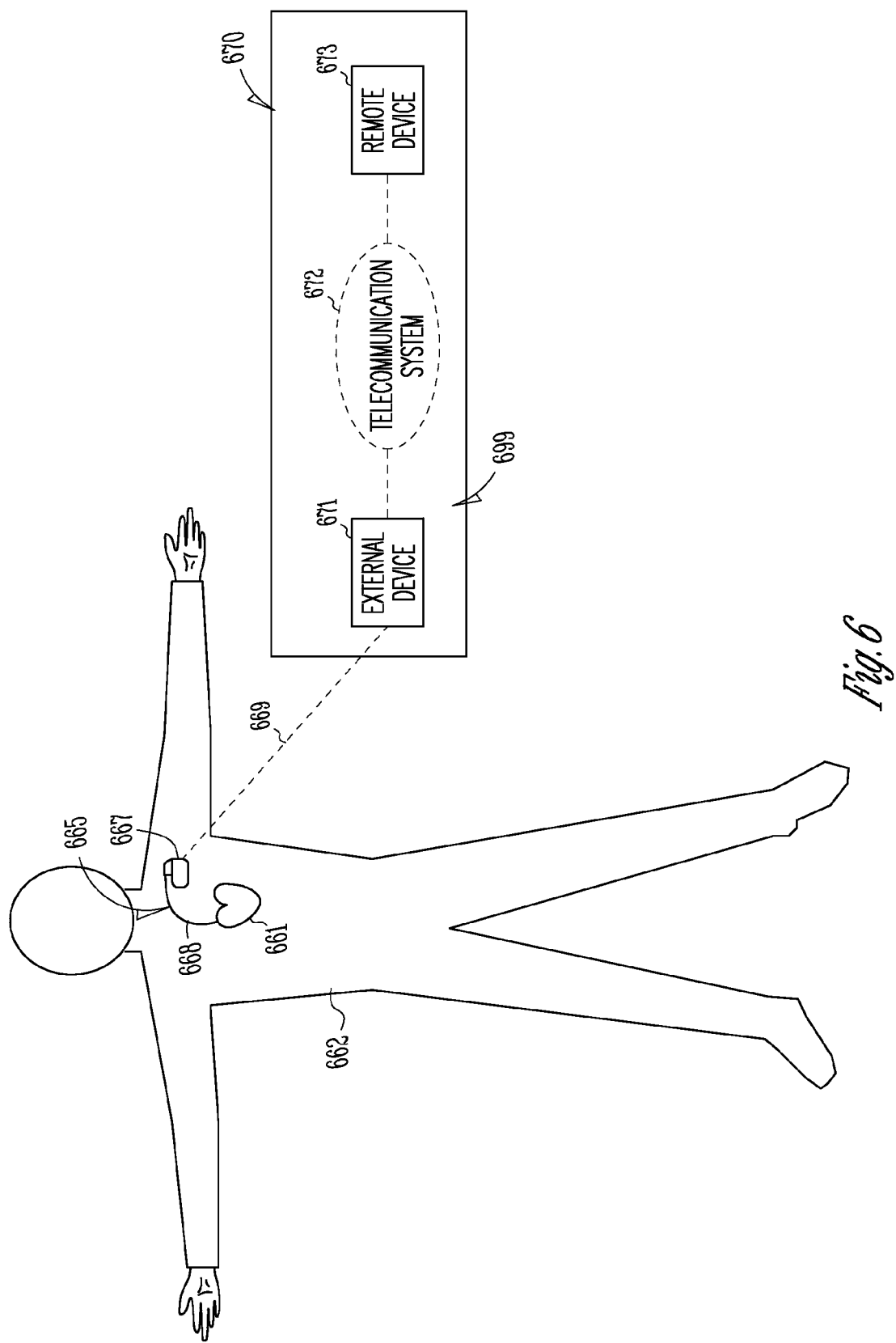
FIG. 6 is an illustration of an embodiment of portions of a cardiac rhythm management system incorporating the heart sound processing system of FIG. 1, and portions of an environment in which it is used.

FIG. 6 is an illustration of an embodiment of portions of a cardiac rhythm management system 699 incorporating heart sound processing system 100, and portions of an environment in which it is used. In one embodiment, cardiac rhythm management system 699 includes an implantable system 665, an external system 670, and a telemetry link 669 providing for communication between implantable system 665 and external system 670.

Implantable system 665 includes an implantable device 667 and a lead system 668. Implantable device 667 is implanted within a patient's body 662 and electrically connected to the patient's heart 661 via lead system 668. Examples of implantable device 667 include pacemakers, cardioverter/defibrillators, pacemaker/defibrillators, cardiac resynchronization devices, cardiac remodeling control devices, and drug delivery devices.

In one embodiment, external system 670 includes an external device 671 in proximity of implantable device 667, a remote device 673 in a relatively distant location, and a telecommunication system 672 linking external device 671 and remote device 673. An example of such an external system includes an advanced patient management system discussed in U.S. patent application Ser. No. 10/323,604, entitled "ADVANCED PATIENT MANAGEMENT FOR DEFINING, IDENTIFYING AND USING PREDETERMINED HEALTH-RELATED EVENTS," filed on Dec. 18, 2002, published as US 20040122484, assigned to Cardiac Pacemakers, Inc., the specification of which is incorporated herein by reference in its entirety. In another embodiment, external system 670 includes an implantable medical device programmer.

In one embodiment, telemetry link 669 is an inductive telemetry link. In an alternative embodiment, telemetry link 669 is a far-field radio-frequency telemetry link. In one embodiment, telemetry link 669 provides for data transmission from implantable device 667 to external device 671. This may include, for example, transmitting real-time physiological data acquired by implantable device 667, extracting physiological data acquired by and stored in implantable device 667, extracting therapy history data stored in implantable device 667, and extracting data indicating an operational status of implantable device 667 (e.g., battery status and lead impedance). In a further embodiment, telemetry link 669 provides for data transmission from external device 671 to implantable device 667. This may include, for example, programming implantable device 667 to acquire physiological data, programming implantable device 667 to perform at least one self-diagnostic test (such as for a device operational status), and programming implantable device 667 to deliver at least one therapy.

In one embodiment, programming implantable device 667 includes sending therapy parameters to implantable device 667. The therapy parameters provide an improved hemodynamic performance for a patient by delivering cardiac pacing pulses to the patient's heart. In one embodiment, the therapy parameters providing for the improved hemodynamic performance are determined by monitoring one or more ventricular diastolic hemodynamics as indicated by parameters related to heart sounds. Such parameters indicate the heart's mechanical activities and electromechanical association. In one specific embodiment, the parameters related to heart sounds are measured by heart sound processing system 100, as discussed above with reference to FIGS. 1-3.

Figure 7:
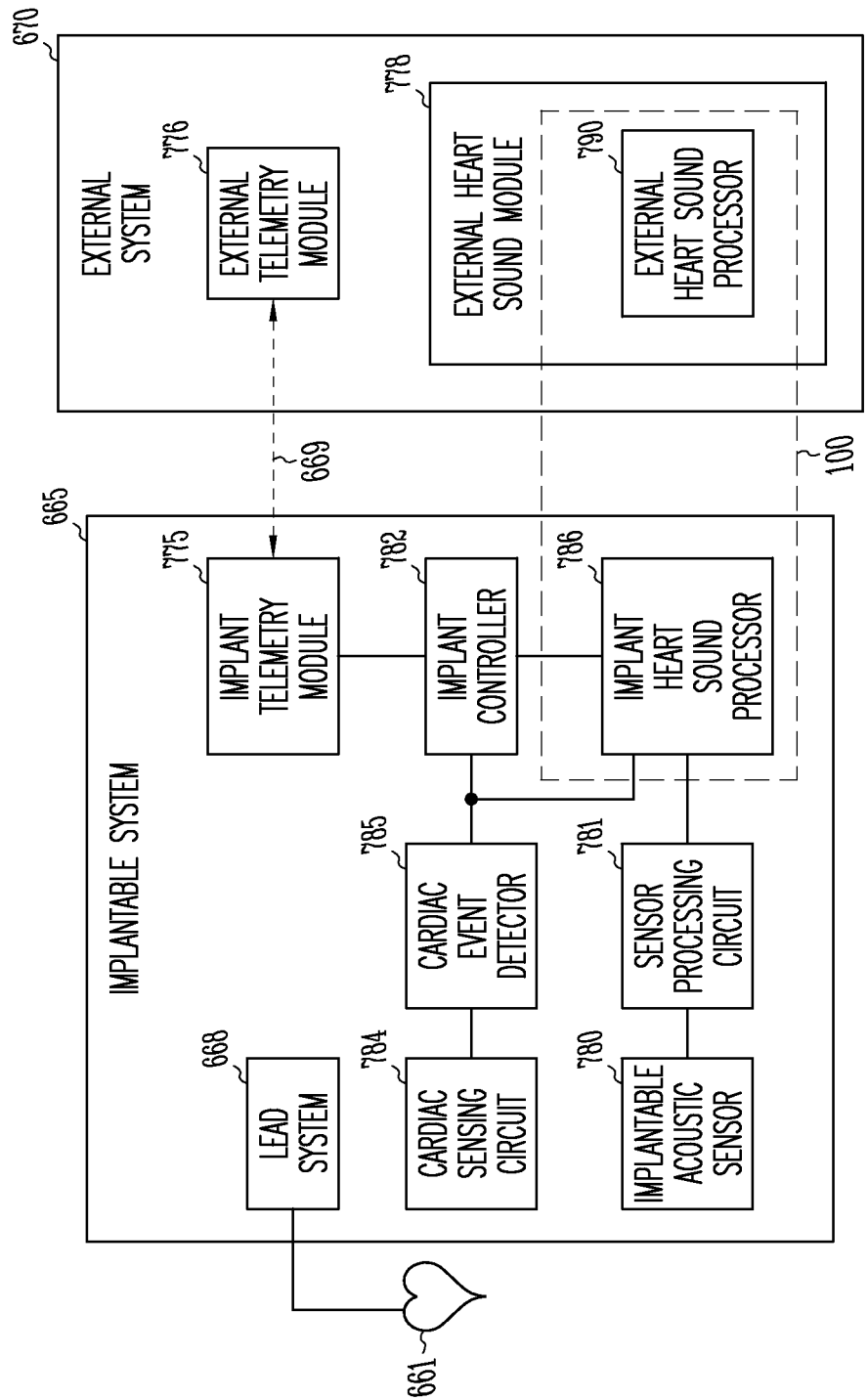
FIG. 7 is a block diagram illustrating a specific embodiment of portions of the cardiac rhythm management system of FIG. 6.

FIG. 7 is a block diagram illustrating a specific embodiment of portions of cardiac rhythm management system 699. Cardiac rhythm management system 699 includes implantable system 665, external system 670, and a telemetry link 669 wirelessly coupling these two systems. Heart sound processing system 100 is included in implantable system 665 and/or external system 670. The actual distribution of heart sound processing system 100 in implantable system 665 and/or external system 670 depends on practical considerations such as power and size constraints of an implantable device, telemetry capability, and systemic factors such as efficiency of operation and convenience of use of cardiac rhythm management system 699. In one embodiment, implantable system 665 includes the entire heart sound processing system 100. In another embodiment, external system 670 includes the entire heart sound processing system 100. In another embodiment, implantable system 665 includes portions of heart sound processing system 100 and external system 670 includes the remaining portions of heart sound processing system 100.

Implantable system 665 includes implantable device 667 and lead system 668. Lead system 668 electrically connects implantable device 667 to heart 661. In one embodiment, implantable device 667 includes a hermetically sealed can to house an implantable acoustic sensor 780, a sensor processing circuit 781, a cardiac sensing circuit 784, a cardiac event detector 785, an implant controller 782, an implant heart sound processor 786, and an implant telemetry module 775. In another embodiment, implantable acoustic sensor 780 is incorporated into a lead of lead system 668. Implantable acoustic sensor 780 senses the acoustic signal indicative of the heart's mechanical vibrations, i.e., heart sounds, of heart 661. In one embodiment, implantable acoustic sensor 780 includes an accelerometer. In another embodiment, implantable acoustic sensor 780 includes a microphone. Sensor processing circuit 781 preconditions the sensed acoustic signal for further processing by heart sound processing system 100. In one embodiment, the acoustic signal is envelope detected. Sensor processing circuit 781 includes a rectifier and a low-pass filter to perform the envelope detection. Cardiac sensing circuit 784 includes sense amplifiers and filters to sense one or more electrograms. In one embodiment, cardiac sensing circuit 784 senses at least a ventricular electrogram indicative of ventricular events including intrinsic ventricular contractions and ventricular pacing pulse deliveries. Cardiac event detector 785 detects predetermined types of cardiac events. In one embodiment, cardiac event detector 785 detects the ventricular events including the intrinsic ventricular contractions and the ventricular pacing pulse deliveries. In one embodiment, cardiac event detector 785 generates event markers to represent the detected events. The event markers each indicate an occurrence, a timing of the occurrence, and a type of the detected event represented. Implant controller 782 controls the overall operation of implantable system 665. In one embodiment, implant heart sound processor 786 includes at least a portion of heart sound processing system 100. In one specific embodiment, implant heart sound processor 786 includes substantially the entire heart sound processing system 100. Implant telemetry module 775 is the portion of the circuit supporting telemetry link 669 that resides in implantable system 665.

External system 670 includes an external telemetry module 776 and an external heart sound module 778. External telemetry module 776 is the portion of the circuit supporting telemetry link 669 that resides in external system 670. External heart sound module 778 includes an external heart sound processor 790. In one embodiment, external heart sound processor 790 includes at least a portion of heart sound processing system 100. In one specific embodiment, external heart sound processor 790 includes substantially the entire heart sound processing system 100. In one embodiment, external heart sound processor 790 is substantially included in external device 671 of external system 670. In another embodiment, external heart sound processor 790 is substantially included in remote device 673 of external system 670. In another embodiment, external heart sound processor 790 is distributed in both external device 671 and remote device 673.

In one embodiment, in addition to the functions of external heart sound processor 790, external heart sound module 778 analyzes parameters derived from detected cardiac events and heart sounds. Examples of such analyses are discussed in U.S. patent application Ser. No. 10/307,896, "PHONOCARDIOGRAPHIC IMAGE-BASED ATRIOVENTRICULAR DELAY OPTIMIZATION," filed Dec. 12, 2002, and U.S. patent application Ser. No. 10/334,694, entitled "METHOD AND APPARATUS FOR MONITORING OF DIASTOLIC HEMODYNAMICS," filed Dec. 30, 2002, now issued as U.S. Pat. No. 7,972,275, both assigned to Cardiac Pacemakers, Inc., the specifications of which are incorporated herein by reference in their entirety.

It is to be understood that the above detailed description is intended to be illustrative, and not restrictive. For example, heart sound processing system 100 may be incorporated into any implanted or external medical device providing for ECG and heart sound monitoring. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A system for detecting heart sounds from an acoustic signal indicative of heart sounds including first heart sounds (S1), second heart sounds (S2), and third heart sounds (S3), the system comprising:

an S3 detector configured to receive the acoustic signal, an S3 threshold, and S3 windows and detect S3 using the acoustic signal and the S3 threshold during the S3 windows;

a measurement module configured to receive the acoustic signal and detect an acoustic energy using the acoustic signal, the acoustic energy being a total acoustic energy of the acoustic signal over a specified time interval; and an S3 threshold generator configured to normalize the S3 threshold using the detected acoustic energy.

2. The system of claim 1, wherein the measurement module is configured to detect a total acoustic energy during a cardiac cycle, and the S3 threshold generator is configured to dynamically normalize the S3 threshold using the total acoustic energy during the cardiac cycle.

3. The system of claim 1, wherein the measurement module is configured to detect a total acoustic energy during systole of a cardiac cycle, and the S3 threshold generator is configured to dynamically normalize the S3 threshold using the total acoustic energy during the systole of the cardiac cycle.

4. The system of claim 1, further comprising:
an S2 detector configured to detect S2 using the acoustic signal; and
an S3 window generator configured to generate the S3 windows each in response to a detection of S2.

5. The system of claim 4, further comprising an S1 detector configured to detect S1.

6. The system of claim 5, wherein the measurement module is configured to detect an amplitude of S1 and an amplitude of S2, the S2 detector is configured to detect S2 using the acoustic signal and an S2 threshold, and the S2 detector comprises an S2 threshold generator configured to determine the S2 threshold using the detected amplitude of S1 and the detected amplitude of S2.

7. The system of claim 1, comprising an implantable medical device including the S3 detector, the measurement module, and the S3 threshold generator.

8. A system for detecting heart sounds from an acoustic signal indicative of heart sounds including first heart sounds (S1), second heart sounds (S2), and third heart sounds (S3), the system comprising:
an S3 detector configured to receive the acoustic signal, an S3 threshold, and S3 windows and detect S3 using the acoustic signal and the S3 threshold during the S3 windows;
a measurement module configured to receive the acoustic signal and detect an acoustic energy using the acoustic signal;
an S3 threshold generator configured to normalize the S3 threshold using the detected acoustic energy; and
an averaging circuit configured to improve a signal-to-noise ratio of the acoustic signal by ensemble averaging.

9. The system of claim 8, further comprising a cardiac signal input to receive a cardiac signal indicative of ventricular events, and wherein the averaging circuit is configured to align segments of the acoustic signal using the ventricular events.

10. The system of claim 8, wherein the averaging circuit is configured to align segments of the acoustic signal using the detected S2.

11. A method for detecting heart sounds from an acoustic signal indicative of heart sounds including first heart sounds (S1), second heart sounds (S2), and third heart sounds (S3), the method comprising:
receiving the acoustic signal;
detecting an acoustic energy by integrating the acoustic signal over a specified time interval;
receiving an S3 threshold;
dynamically normalizing the S3 threshold using the detected acoustic energy;
receiving S3 windows; and
detecting S3 using the acoustic signal and the S3 threshold during the S3 windows.

12. The method of claim 11, wherein detecting the acoustic energy comprises detecting a total acoustic energy during a cardiac cycle.

13. The method of claim 11, wherein detecting the acoustic energy comprises detecting a total acoustic energy during systole of a cardiac cycle.

14. The method of claim 11, further comprising performing ensemble averaging of the acoustic signal, and detecting the S3 using the ensemble-averaged acoustic signal and the S3 threshold during the S3 windows.

15. The method of claim 11, further comprising:
detecting S2 using the acoustic signal; and
generating the S3 windows each in response to a detection of S2.

16. The method of claim 15, wherein generating the S3 windows comprises generating the S3 windows each after a predetermined delay starting with the detection of S2.

17. The method of claim 16, further comprising detecting S1 using the acoustic signal.

18. The method of claim 17, wherein detecting S2 comprises:
detecting an amplitude of S1;
detecting an amplitude of S2;
determining an S2 threshold using the detected amplitude of S1 and the detected amplitude of S2; and
detecting S2 using the acoustic signal and the S2 threshold.

19. The method of claim 18, wherein detecting S2 comprises detecting S2 using the acoustic signal and the S2 threshold during S2 windows, and further comprising:
detecting ventricular events from a cardiac signal; and
generating the S2 windows each after a predetermined delay starting with a detection of the ventricular events.

20. The method of claim 11, comprising sensing the acoustic signal using an implantable sensor.

* * * * *